(12) United States Patent
Chamberlain et al.

(10) Patent No.: US 10,871,475 B2
(45) Date of Patent: Dec. 22, 2020

(54) AUTOMATED TITRATION IN A RECIRCULATING FLUID SYSTEM

(71) Applicant: BECS Technology, Inc., St. Louis, MO (US)

(72) Inventors: Roger Chamberlain, Creve Coeur, MO (US); Chris Edmiston, Fairview Heights, IL (US); Brett Steinbrueck, St. Louis, MO (US); Don Williams, High Ridge, MO (US)

(73) Assignee: BECS TECHNOLOGY, INC., St. Louis, MO (US)

(*) Notice: Subject to any disclaimer, the term of this patent is extended or adjusted under 35 U.S.C. 154(b) by 155 days.

(21) Appl. No.: 16/141,396

(22) Filed: Sep. 25, 2018

(65) Prior Publication Data
US 2019/0025267 A1    Jan. 24, 2019

Related U.S. Application Data

(63) Continuation-in-part of application No. PCT/US2018/018663, filed on Feb. 20, 2018, which
(Continued)

(51) Int. Cl.
*G01N 31/16* (2006.01)
*G01N 33/18* (2006.01)
(Continued)

(52) U.S. Cl.
CPC .......... *G01N 31/166* (2013.01); *C02F 1/008* (2013.01); *C02F 1/66* (2013.01); *G01N 31/221* (2013.01);
(Continued)

(58) Field of Classification Search
CPC ........ C02F 1/008; C02F 1/66; C02F 2103/42; C02F 2209/005; C02F 2209/04;
(Continued)

(56) References Cited

U.S. PATENT DOCUMENTS 4,931,187 A    6/1990  Derham et al.
5,389,546 A    2/1995  Becket
(Continued)

FOREIGN PATENT DOCUMENTS

CN    103217412    7/2013
EP       1953120    8/2008

OTHER PUBLICATIONS

Katsumata et al. Talanta, vol. 48, 1999, pp. 135-141.*
Patent Cooperation Treaty, International Search Report for PCT/US2018/018663, 3 pages dated Jun. 4, 2018.

*Primary Examiner* — Maureen Wallenhorst
(74) *Attorney, Agent, or Firm* — Bryan Cave Leighton PaisnerLLP

(57) ABSTRACT

A method for determining a concentration of a chemical of interest in a recirculating analyte system includes the steps of selecting a first indicator threshold, measuring the flow rate of the recirculating analyte system, controllably adding a known amount of reagent to the recirculating analyte system at an known flow rate, repetitively measuring an indicator of the recirculating analyte system downstream from the addition of the reagent, and computing the concentration of the chemical of interest of the recirculating analyte system when the indicator measurement crosses the indicator threshold.

17 Claims, 7 Drawing Sheets

Related U.S. Application Data is a continuation-in-part of application No. 15/438,391, filed on Feb. 21, 2017, now Pat. No. 10,018,610.

(51) Int. Cl.

| | | |
|---|---|---|
| *G01N 31/22* | (2006.01) | |
| *G01N 35/00* | (2006.01) | |
| *C02F 1/66* | (2006.01) | |
| *C02F 1/00* | (2006.01) | |
| C02F 103/42 | (2006.01) | |
| G01N 27/416 | (2006.01) | |
| G01N 35/10 | (2006.01) | |

(52) U.S. Cl.
CPC ....... *G01N 33/18* (2013.01); *G01N 35/00663* (2013.01); *C02F 2103/42* (2013.01); *C02F 2209/005* (2013.01); *C02F 2209/04* (2013.01); *C02F 2209/06* (2013.01); *C02F 2209/07* (2013.01); *C02F 2209/40* (2013.01); *C02F 2303/14* (2013.01); *G01N 27/4167* (2013.01); *G01N 27/4168* (2013.01); *G01N 35/1002* (2013.01); *G01N 2035/00673* (2013.01)

(58) Field of Classification Search
CPC ............. C02F 2209/06; C02F 2209/07; C02F 2209/40; C02F 2303/14; G01N 2035/00673; G01N 27/4167; G01N 27/4168; G01N 31/16; G01N 31/166; G01N 31/221; G01N 33/18; G01N 33/1813; G01N 35/00663; G01N 35/1002
USPC ................... 436/39, 52, 163; 422/75, 82.12
See application file for complete search history.

(56) References Cited

U.S. PATENT DOCUMENTS

| | | | |
|---|---|---|---|
| 8,404,117 | B1 | 3/2013 | Steinbrueck et al. |
| 9,347,922 | B2 | 5/2016 | Dugstad et al. |
| 9,349,614 | B2 | 5/2016 | Wang et al. |
| 10,018,610 | B1* | 7/2018 | Chamberlain ............ C02F 1/00 |
| 2002/0151080 | A1* | 10/2002 | Dasgupta ............. G01N 31/166 |
| | | | 436/55 |
| 2004/0023405 | A1* | 2/2004 | Bevan ................. G01N 31/166 |
| | | | 436/163 |
| 2009/0200245 | A1* | 8/2009 | Steinbrueck ............ C02F 1/008 |
| | | | 210/741 |
| 2010/0210026 | A1 | 8/2010 | Hintz et al. |
| 2017/0248568 | A1* | 8/2017 | Yizhack .................... G01J 3/42 |
| 2019/0317063 | A1* | 10/2019 | Kraus .................... G01N 31/16 |

* cited by examiner

AUTOMATED TITRATION IN A RECIRCULATING FLUID SYSTEM

RELATED APPLICATIONS

This application is a continuation-in-part and claims priority to International Application No. PCT/US2018/018663, filed on Feb. 20, 2018, which PCT application claims priority to U.S. patent application Ser. No. 15/438,391, filed on Feb. 21, 2017, now U.S. Pat. No. 10,018,610.

FIELD OF THE INVENTION

This invention relates generally to methods and systems for performing titrations in a recirculating fluid system and, more particularly, measuring the chemical properties of flowing water in a body of water without adversely impacting the chemistry of the water

BACKGROUND OF THE INVENTION

Titration is a process to assess chemical properties of aqueous solutions or for determining an unknown property (typically concentration) of an analyte. In a regular titration, a known quantity of the analyte (sample) is in a mixing vessel and a reagent is added (e.g., via a calibrated burette) until the balance point is reached. Frequently this is determined by a color change due to an indicator, added to the analyte prior to the titration. With knowledge of the quantity of analyte, quantity of reagent, and reagent concentration, one can determine the analyte concentration.

Consider the reaction $n_S S + n_R R \rightarrow P$, where S is the analyte, R is the reagent, P is the product, and $n_S$ and $n_R$ are the stoichiometric coefficients of the analyte sample and the reagent, respectively. It is known to perform a flow titration by mixing the reagent at flow rate $f_R$ with the analyte at flow rate $f_S$. The equivalence condition is given by: $C^S \cdot f_S / n_S = C^R \cdot f_R / n_R$, where $C^S$ is the concentration of the analyte S and $C^R$ is the concentration of the reagent R. By controlling the reagent flow rate, $f_R$, to reach equivalence, the knowledge of reagent concentration, $C^R$, sample flow rate, $f_S$, reagent flow rate, $f_R$, and coefficients $n_S$ and $n_R$ allows one to determine $C^S$, the unknown sample concentration.

This conventional method works well for a still body of water. However, in certain applications, including most aquatic applications, specifically a recirculating water system, a chemical property for a flowing stream of water is required. When the water is recirculated, as in aquatic applications, special care must be taken in performing the measurement. Adding a reagent to a recirculating system for the purpose of measuring water chemistry can adversely affect the chemical balance of the entire body of water, especially in small bodies of water such as spas and slash pads. For a recirculating water system the output flow will be returned to the larger body of water and, therefore, there is a need for a system and method which minimizes the quantity of reagent used.

SUMMARY OF THE INVENTION

According to one aspect of the present invention, a method for determining a concentration of a chemical of interest in a recirculating analyte system, wherein the analyte having a known stoichiometric coefficient of $n_S$, includes the steps of selecting a first indicator threshold, measuring a flow rate of the recirculating analyte system ($f_S$), controllably adding a known amount of reagent having a stoichiometric coefficient of $n_R$ and has a reagent concentration $C^R$ to the recirculating analyte system at an reagent flow rate ($f_R$), repetitively measuring an indicator of the recirculating analyte system downstream from the addition of the reagent, and computing the concentration of the chemical of interest in the recirculating analyte system when the indicator crosses the indicator threshold, wherein the concentration of the chemical of interest of the recirculating analyte system is computed as: $C^S = C^R \cdot n_S / n_R \cdot f_R / f_S$.

The method may be used in situations where the analyte is an acid, the reagent is a base, and the indicator is pH. The method may also be used where the analyte is a base, the reagent is an acid, and the indicator is pH. In addition, the method may be used in situations where the analyte is a reducing agent, the reagent is an oxidizing agent, and the indicator is oxidation-reduction potential ("ORP"). Finally, the method may be used where the analyte is an oxidizing agent, the reagent is a reducing agent, and the indicator is ORP.

The step of controllably adding a known amount of reagent to the recirculating water system can be accomplished in a number of ways, including, adding reagent at an initial reagent flow rate ($f_{A,INIT}$) and, until the indicator measurement crosses the indicator threshold, repetitively waiting a period of time, measuring the indicator of the recirculating water system, and increasing the reagent flow rate by a fixed increment. An alternative method for controllably adding reagent to the recirculating water system includes adding regent at an initial reagent flow rate, monitoring the measured indicator until the measured indicator exhibits an exponential response, and extrapolating a stable indicator reading based on the exponential response.

The present invention also includes a device for determining a concentration of a chemical of interest in a recirculating analyte system, the analyte having a stoichiometric coefficient of $n_S$. Preferably, the device includes an intake port to receive a sample of the analyte, a flow rate meter for measuring the flow rate of the sample of the analyte system ($f_S$), a vessel holding a reagent having a stoichiometric coefficient of $n_R$, a pump for controllably adding reagent from the vessel into the sample of the analyte at an reagent flow rate ($f_R$), tubing for transferring the reagent from the pump to the sample of the analyte, a probe for repetitively measuring an indicator of the recirculating analyte system downstream from the addition of the reagent, and a computing element for computing the concentration of the chemical of interest in the recirculating analyte system. Preferably, the computing element computes the concentration when the indicator measurement crosses an indicator threshold, and the concentration of the chemical of interest of the recirculating analyte system is computed as: $C^S = C^R \cdot n_S / n_R \cdot f_R / f_S$.

BRIEF DESCRIPTION OF THE FIGURES

These and other features, aspects and advantages of the invention will become more fully apparent from the following detailed description, appended claims, and accompanying drawings, wherein the drawings illustrate features in accordance with an exemplary embodiment of the present invention, and wherein:

DETAILED DESCRIPTION OF THE INVENTION

Figure 1:
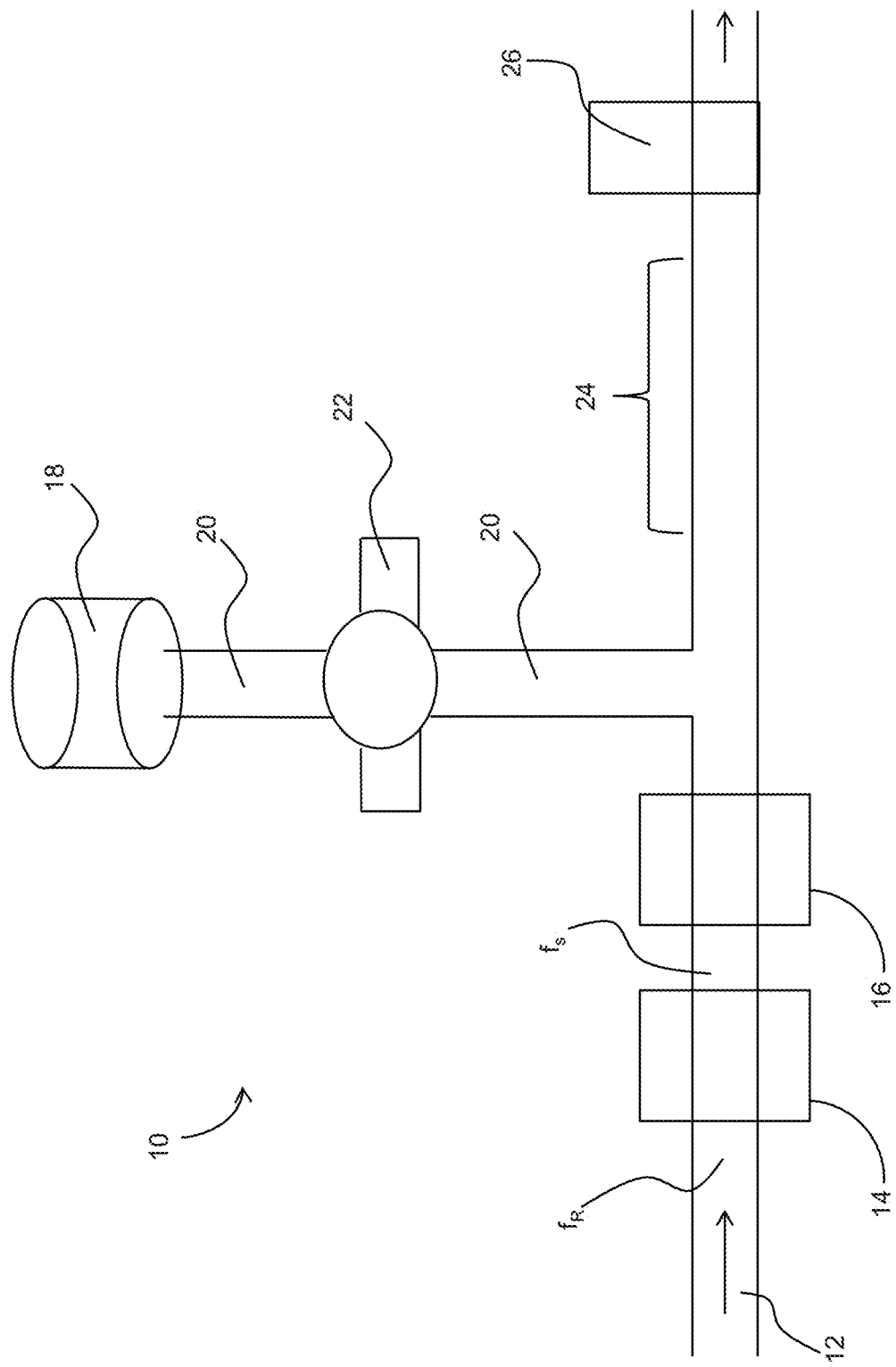
FIG. 1 is a block diagram illustrating the principal components of an embodiment of the system for determining the total alkalinity of a flowing body of fluid.
Figure 2:
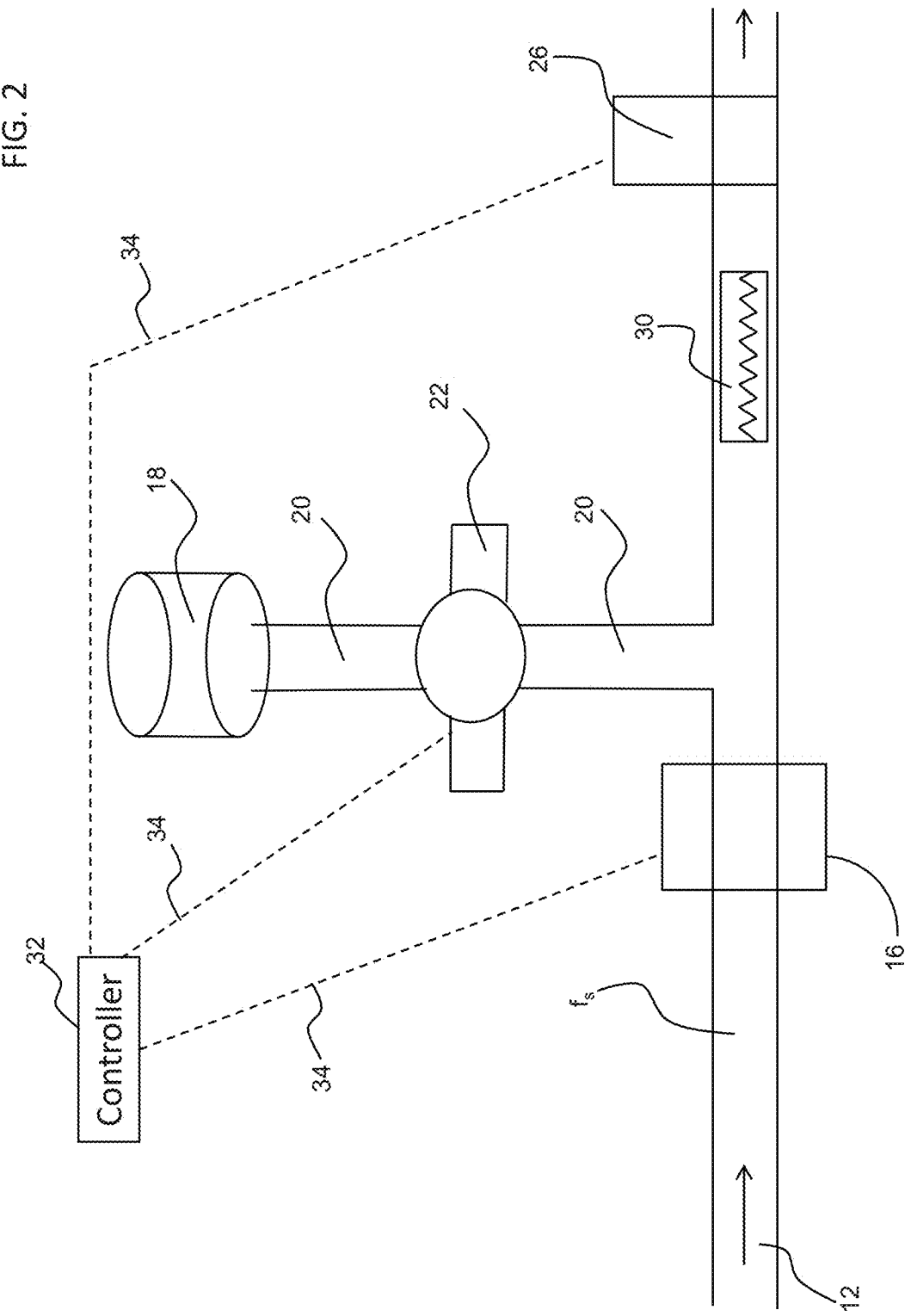
FIG. 2 is a block diagram illustrating the principal components of another embodiment of the system for determining the total alkalinity of a flowing body of fluid.

Referring to FIGS. 1 and 2, the principle components of a system 10 for determining the total alkalinity of a recirculating water system are illustrated. The system 10 may be used in connection with the operation of any form of aquatic facility, for example, a family water recreation facility that may include features such as a swimming pool, a spa, whirlpool, and other features such as water jets, water slides, river rapid rides, waterfalls, decorative fountains, spillways, buckets, lazy rivers, and the like. The system and the methods described below allow one to modify the standard titration technique using fixed volumes of water to calculate total alkalinity with known flow rates in a flowing stream.

In one embodiment illustrated in FIG. 1, the system 10 includes tubing 12 for at least a sample of the water to be analyzed to flow, a flow rate regulator 14 that can alter the flow rate of the water, and a flow rate meter 16 for measuring the water flow rate. A second section of tubing 20 is coupled to the tubing 12 downstream of the flow rate meter 16. An acid, for example muriatic acid stored in vessel 18, flows into the stream of water as controlled by a precision metering pump 22, which pumps at a set rate $f_A$. The stream of water and the added acid are combined in a mixing section 24 configured to ensure adequate mixing downstream from the intersection of tubing 12 and the second section of tubing 20. The system further includes a pH probe 26 to measure the acidity of the stream of water. Certain of these components may be controlled by a computer-based controller 32 as shown in FIG. 2. Thus, the flow rate meter 16 and the pH probe 26 may send signals 34 to the controller 32 that represent the flow rate and the pH of the flowing water respectfully. The controller 32 may send a signal 34 to the pump 22 to control the addition of acid to the flowing water.

The sample stream of water to be measured enters the tubing 12 from the left end as depicted in FIGS. 1 and 2. As needed, the flow rate regulator 14 regulates the flow of the water to a certain flow rate $f_R$. The flow rate of the stream of water, $f_S$, is then measured by the flow rate meter 16. If $f_S < f_R$, there is insufficient pressure differential above and below the flow regulator 14 for it to operate effectively. An alternative approach is to monitor the sample stream flow rate (instead of including a flow regulator) and to not perform an alkalinity reading if the sample stream flow rate is not in an appropriate range.

The muriatic acid to be added is fed via precision metering pump 22, which may be set by the controller 32. The combination of the sample stream and the added acid flow into the mixing section 24 configured to ensure adequate mixing. The mixing section 24 may include mechanical elements to create turbulence to mix the sample stream and the acid. Optionally, a mixer 30, such as an auger created on a 3D printer, can be included in this length of tubing 24. Downstream of the mixing, the pH of the stream is measured by the pH probe 26 and a signal indicative of the pH is sent to the controller 32.

Preferably, the muriatic acid is sufficiently strong as to have a pH below the threshold chosen below. The concentration used for calibration is preferably maintained for subsequent readings; however, the specific concentration is not crucial, as long as there is sufficient controllability of flow rates by the metering pump 22, and the concentration is consistent between the calibration and the later readings by the pH probe 26.

The operation of performing a reading of the total alkalinity may now be described. First, a pH threshold is chosen, preferably between 4.0 and 5.0 pH. This threshold value is labeled $Th_{pH}$. The metering pump 22 precisely controls the delivery of acid at a rate that takes the pH reading at or just below $Th_{pH}$. There are a number of possible methods to accomplish this as described below.

When the pH reading is at or just below $Th_{pH}$, the sample flow rate $f_S$ and the acid flow rate $f_A$ are recorded by the controller 32. The total alkalinity (TA) may then be computed as follows:

$$TA = K_{CAL} \times \left(\frac{f_A}{f_S}\right),$$

where $K_{CAL}$ is a calibration constant defined below.

The determination of the calibration constant $K_{CAL}$ preferably uses the inverse of the above equation. The method includes recording $f_S$ and $f_A$. The total alkalinity is measured using an independent method, for example, a color test method or other suitable conventional method. The calibration constant, $K_{CAL}$, may then be computed as $$K_{CAL} = TA \times \left(\frac{f_S}{f_A}\right).$$

In many uses, the systems and methods described herein are used in conjunction with a large aquatic facility, such as a municipal swimming pool or water park. The aquatic facility many include a master controller such as a BECSys 7 controller commercially available through BECS Technology, Inc. of St. Louis, Mo. As is known in the industry, the master controller may measure the pH, temperature, and total dissolved solids of the water in the aquatic facility, as well as control the discharge of chemicals into the water. The components illustrated in FIGS. 1 and 2 preferably may be located remote from the master controller. The calibration of the pH reading can take advantage of the fact that the pH in the sample stream with the acid pump off (i.e., not delivering any acid) will be approximately equal to the pH of the water in the vicinity of the master controller. As such, the local pH calibration can be tied to the pH reading of the master controller. This can be accomplished via any traditional, single-point calibration technique, in which the individual reading used for calibration (which comes from the master controller) is used to adjust either the slope or the offset of a linear calibration.

For example, when reading a sensor with a linear response, the transformation function (i.e., the conversion function) may have the following form: pHval=m× ADCval+b, where ADCval is the input value from an analog-to-digital converter, pHval is the value of the current pH reading (corresponding to the input ADCval), m is the conversion slope, and b is the offset of the conversion. Single point calibration of the slope uses an independent pH reading (e.g., from the master controller), pHval$_{CAL}$, a current analog-to-digital converter input value, ADCval$_{CAL}$, and b to compute a new (calibrated) slope:

$$m = \frac{pHval_{CAL} - b}{ADCval_{CAL}}.$$

Single point calibration of the offset uses an independent pH reading (e.g., from the master controller), pHval$_{CAL}$, a current analog-to-digital converter input value, ADCval$_{CAL}$, and m to compute a new (calibrated) offset: b=pHval$_{cAL}$−m×ADCval$_{CAL}$.

During either a reading or a calibration, the controller 32 preferably controls the acid pump so as to deliver acid at a rate that takes the pH reading at or just below Th$_{pH}$. This may be accomplished in a number of ways to avoid adversely impacting the pH of the body of water. In a first method, a linear progression technique starts at a fixed (slow) pump rate, f$^{A,INIT}$. After waiting a sufficient time for the pH reading to stabilize, for example, about 120 seconds, the pH value is read by the controller 32. If the pH reading is ≤Th$_{PH}$, then f$_A$ is set to the current pump rate. If the pH reading is greater than Th$_{pH}$, the pump rate is increased by a fixed increment, f$_{A,INC}$ and the process returns back to waiting a sufficient time for the pH reading to stabilize and reading the pH value.

Another embodiment includes steps to determine when the pH reading has stabilized. This embodiment includes comparing the difference between two successive pH readings and, when the difference falls below a chosen difference threshold for a set duration of time, setting f$_A$ equal to the acid flow rate at that time. This embodiment would include selecting a difference threshold, for example 0.01 pH, and selecting the set duration of time, for example, 20 seconds.

An alternative technique is a fast linear progression, in which the pH probe 26 reads the pH at a higher sampling rate. The process waits a sufficient time for the exponential response of the pH measurement to become evident in the pH samples. The stable pH reading is extrapolated from the initial exponential curve in the pH samples. If the stable pH reading is ≤Th$_{pH}$, then f$_A$ is set to the current pump rate. If the stable pH reading is greater than Th$_{pH}$, the pump rate is increased by a fixed increment, f$_{A,INC}$ and the process returns back to waiting a sufficient time for the exponential response of the pH measurement to become evident in the pH samples, and extrapolating the pH value.

For example, a system with an exponential time response can be expressed using the following formula: val(t)=val$_F$+(val$_{INIT}$−val$_F$)×e$^{−(t/\tau)}$, where val$_{INIT}$ is the initial value, val$_F$ is the final value, and T is the time constant of the system (pH probe in our case). By taking several readings of val(t), appropriate software can perform a least mean squares curve fit to the above equation, for the purpose of estimating the final value V$_F$.

A third method for controlling the delivery of acid is a binary progression technique. The sequence of steps is the same as for linear progression, except instead of a regular increment in the acid pump rate, f$_{A,INC}$, the pump rate follows a binary search pattern. For example, two values may be initialized to the minimum, f$_{A,MIN}$, and maximum, f$_{A,MAX}$, acid feed rates supported by the pump (or alternatively, some narrower search range). The acid feed rate f$_A$ is set to the mid-point between f$_{A,MIN}$ and f$_{A,MAX}$:

$$f_A = \frac{f_{A.MIN} + f_{A.MAX}}{2}.$$

Then, the pH reading (either value at end of delay period or extrapolated from exponential response) is compared to threshold Th$_{pH}$. If the pH value is within a tolerance, ε, of the threshold (e.g., Th$_{pH}$−ε≤pHval≤Th$_{pH}$+ε), the current feed rate f$_A$ is the feed rate to use to compute total alkalinity. Otherwise, if the pH value is above threshold, set f$_{A,MIN}$←f$_A$ and the process returns to comparing the pH reading. Otherwise, if the pH value is below threshold, set f$_{A,MAX}$←f$_A$ and the process returns to comparing the pH reading. This preferably results in a faster search to find the value of acid feed rate that is near threshold.

In each of the above approaches to controlling the acid, if the pH falls below a lower threshold (Th$_{pHlow}$) before the time period is complete, the reading can be considered finished (with a pH value of Th$_{pHlow}$). A reasonable value for Th$_{pHlow}$ is 4.0.

For a traditional titration process, the volume of water used for the titration is fixed, and although it ends up with a low pH (and therefore must be disposed of safely), it is sufficiently small that simple dilution is fairly easy (e.g., returning it to the pool). For a titration process with flowing water, the volume of water affected by the added acid is potentially much larger, but preferably, the total acid added is small enough that it does not impact the overall pool chemistry. The above-described methods for controlling the delivery of acid, particularly the fast linear progression and binary progression techniques, minimize the overall quantity of acid used to perform the titration.

Another approach to minimizing the impact on pool chemistry is to lower the frequency of the total alkalinity readings (e.g., read alkalinity only once per day, when the pool is closed, to give time for the system to recover from any inadvertent impact). This has a potential to have a detrimental effect on the total alkalinity control, as fewer readings means less knowledge of the current state of the water chemistry while making control decisions (i.e., the total alkalinity control decisions described above).

Yet another approach to minimizing the impact on pool chemistry is to control the timing of the flowing water titration process. For example, the water chemistry controller detects when the pH of the system is high (i.e., above setpoint), and can feed acid to lower the pH in the controlled body of water. This would be an ideal time to perform a flowing water titration, as the titration adds acid as well, and has the benefit of improving system visibility for control purposes.

There are a number of benefits to the automated sensing of alkalinity that accrue to the master controller of the aquatic facility that has overall responsibility for water chemistry. For example, monitoring the chemistry in an aquatic facility is aided when one knows the calcium saturation index (CSI) of the water, which is a measure of the pool water's tendency to scale or corrode. The input factors that determine the saturation index include pH, temperature, total dissolved solids, total alkalinity, and calcium hardness.

Prior to the availability of the total alkalinity reading, the master controller was able to directly measure pH, temperature, and total dissolved solids, while the pool operator was required to manually input the values for total alkalinity and calcium hardness. With the availability of a total alkalinity reading, one of the manual steps required has been eliminated, both lowering labor requirements and increasing accuracy (as manual testing of total alkalinity is an error-prone process).

The master controller preferably has means for reporting its readings both locally and remotely (to remote devices via the Internet). This includes establishing and reporting on out-of-range conditions (i.e., alarms) on these readings. By adding total alkalinity to this set, the ability of pool operators to both understand the chemical state of the pool and to be informed when something is amiss is improved.

While the above description is primarily focused on reading the total alkalinity, it is also desirable to control the alkalinity in a body of water. One approach to alkalinity control is to alter the mechanism for pH control depending upon the alkalinity reading. Alkalinity may be read using the method described above or a convention method such as a colorimetric test and/or manual entry of an alkalinity reading.

There are two mechanisms commonly used for pH control, and many systems have both installed. One is via feeding of carbon dioxide ($CO_2$), and the other is via feeding acid. Generally, feeding $CO_2$ will leave alkalinity unchanged, and feeding acid can lower alkalinity. One preferred approach follows this logic. If alkalinity is above a given threshold (which may be set by the user), pH is controlled by adding acid. Alternatively, if alkalinity is below the threshold, pH is preferably controlled by adding $CO_2$. Yet another preferred embodiment is to proportion the control pH by prorating the addition of $CO_2$ and acid.

A second approach to alkalinity control is to support the feeding of sodium bicarbonate, which has the tendency to raise the alkalinity of the water. The feeding of sodium bicarbonate provides an increase in alkalinity, and the feeding of acid provides a decrease in alkalinity.

Yet another approach is to adjust the mechanism for chlorine control as a mechanism for alkalinity control. Different types of chlorine feed drive alkalinity up vs. down, and similar to the pH control example above, one can adjust the proportion of chlorine feed via one mechanism or another to actively push alkalinity towards its desired range of operation.

In addition to being able to control the alkalinity in a pool, knowledge of the alkalinity can benefit other aspects of the water chemistry control. For example, when alkalinity is very low, the pH is dramatically more sensitive to acid injection, which can motivate the alteration of control parameters (for example, feed slower to reduce overshoot). Similarly, when the alkalinity is very high, the opposite occurs, pH is dramatically less sensitive to acid injection. As a result, one can alter control parameters in the opposite direction (feed acid at a greater rate for pH control).

Many of the techniques described above in connection with a system for computing total alkalinity may be used to determine the concentration of a chemical of interest in an analyte flowing through a recirculating system.

Figure 3:
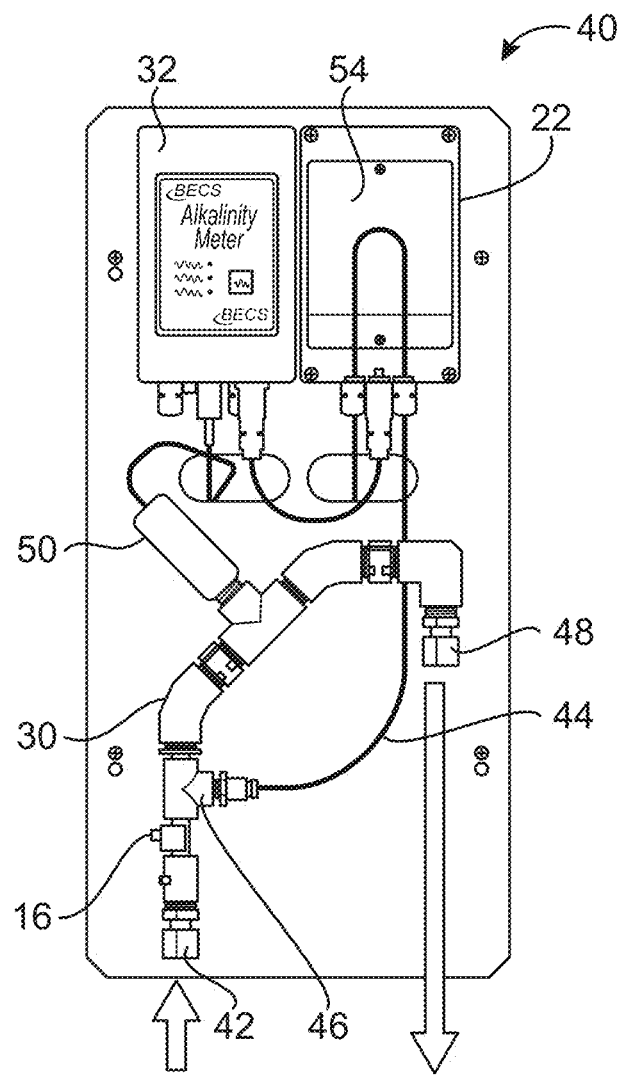
FIG. 3 is an illustration of a device that may be used determining a concentration of a chemical of interest in a recirculating analyte system.

The principles described herein may be used for developing methods and systems for performing titrations in a recirculating fluid stream without adversely impacting the chemistry of the fluid stream. The titrations may be performed using the device 40 shown in FIG. 3. The device 40 includes an input port 42 into which the sample analyte (at flow rate $f_S$) enters. The flow rate of the sample analyte is measured using, for example, a flow rate meter 16. A metering pump 22, for example a precision peristaltic pump, controllably injects reagent (at flow rate $f_R$) from a storage vessel 54 through tubing 44 via a coupler 46 into a mixer 30. The pump 22 includes a set of rollers 52 capable of pinching the tubing 44 in order to stop the flow of reagent into the tubing 44. The reagent is mixed with the sample analyte. An indicator probe 50 located downstream of the mixer 30 measures an indicator of the mixed analyte with reagent. For example, if the analyte is an acid, the reagent is a base, then the indicator is pH. Alternatively, where the analyte is a base, the reagent is an acid, then the indicator is also pH. In both of these situations where the indicator is pH, the indicator probe 50 may be a pH probe. The device 40 may be used in situations where the analyte is a reducing agent, the reagent is an oxidizing agent, and the indicator is ORP. Finally, the device 40 may be used where the analyte is an oxidizing agent, the reagent is a reducing agent, and the indicator is ORP. In both of these latter situations where the indicator is ORP, the indicator probe 50 may be an ORP probe. After mixing and measuring, the mixed analyte/reagent fluid is discharged back into the recirculating system via output port 48. The device includes a controller 32 directing the operation of the entire system. For example, the controller 32 controls the reagent flow pumped from the storage vessel 54 via the pump 22. The pump 22 is controlled by establishing the step rate on the stepper motor driving the pump. The controller 32 also reads the measured sample analyte flow rate and indicator reading. The controller 32 may communicate with a water chemistry controller as described above via, for example, an RS-485 interface.

Figure 4:
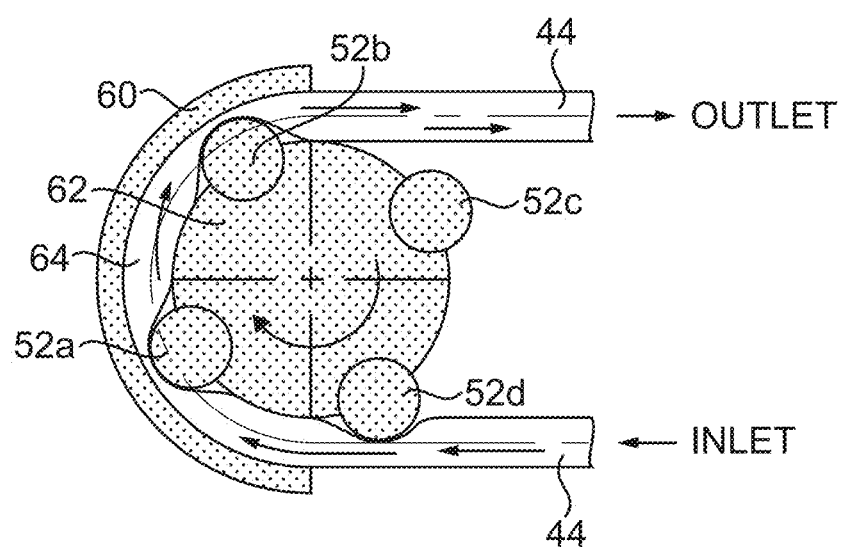
FIG. 4 is an illustration of certain components of a metering pump that may be used with the device of FIG. 3 in certain embodiments.

FIG. 4 illustrates certain components of the metering pump 22. The pump 22 may include an interior supporting surface 60, which supports the tubing 44 between an inlet and an outlet. The pump 22 includes a rotor 62 having a set of rollers 52a-d. In the stationary rotor position illustrated in FIG. 4, the rollers 52a and 52b pinch the tubing 44 against the interior supporting surface 60 in order to prevent the release of reagent into the mixer 30. The rollers 52a and 52b also serve to retain a volume of fluid 64 therebetween. Upon rotation of the rotor, rollers 52a and 52b rotate into the locations shown as 52b and 52c in FIG. 4, thereby releasing the volume of fluid 64 through the outlet of the tubing 44. In this matter, the metering pump 22 releases a set volume of reagent into the tubing 22 with each rotation of the rotor 62.

Of course, the metering pump 22 illustrated in FIG. 4 may be altered in a number of ways, including having a different numbers of rollers 52, having a different size of transferred fluid volume 64, etc.

The device 40 may be used to determine a concentration of a chemical of interest in a recirculating analyte system, the analyte having a stoichiometric coefficient of $n_S$. The method includes the steps of (a) selecting a first indicator threshold; (b) measuring a flow rate of the recirculating analyte system ($f_S$);
(c) controllably adding a known amount of reagent having a stoichiometric coefficient of $n_R$ to the recirculating analyte system at an reagent flow rate ($f_R$), wherein the reagent has a reagent concentration $C^R$; (d) repetitively measuring an indicator of the recirculating analyte system downstream from the addition of the reagent; and (e) computing the concentration of the chemical of interest in the recirculating analyte system when the reagent/analyte mixture reaches equivalence, for example, when the indicator crosses (falls below or rises above) the indicator threshold, wherein the concentration of the chemical of interest of the recirculating analyte system is computed as: $C^S = C^R \cdot n_S/n_R \cdot f_R/f_S$.

Preferably, the concentration of the chemical of interest is calculated when the reagent/analyte mixture reaches equivalence. For example, if the analyte is an acid, the reagent is a base, and the indicator is pH, the calculation would be performed when the pH rises above the indicator threshold. Alternatively, where the analyte is a base, the reagent is an acid, and the indicator is pH, the calculation would be performed when the pH falls below the indicator threshold. If the analyte is a reducing agent, the reagent is an oxidizing agent, and the indicator is ORP, the calculation would be performed when the ORP rises above the indicator threshold. If the analyte is an oxidizing agent, the reagent is a reducing agent, and the indicator is ORP, the calculation would be performed when the ORP falls below the indicator threshold.

Preferably, the device 40 minimizes the amount of reagent used to perform the titration. There are a number of approaches to diminishing reagent use. Described herein are examples of approaches where the analyte is a base, the reagent is an acid, and the indicator is pH. Of course, those skilled in the art will be able to apply these examples to situations where the analyte is an acid and the reagent is a base, as well situations where the analyte is a reducing agent, the reagent is an oxidizing agent and where the analyte is an oxidizing agent and the reagent is a reducing agent.

The most straightforward approach to controlling the reagent flow rate is a linear ramp, increasing the reagent flow rate until the measured pH falls below the target value. A ramp may be approximated via stepwise changes in pump rate to accommodate delays in the response of the indicator probe.

Figure 5:
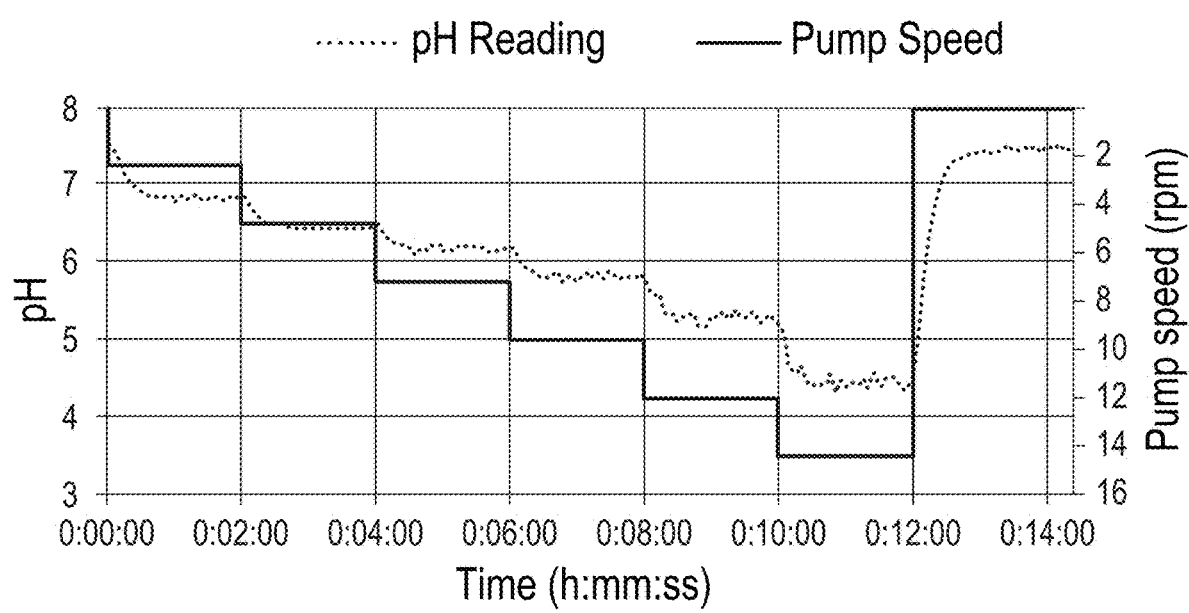
FIG. 5 is a graph illustrating the relationship between pump rates and measured indicator using the device of FIG. 3 in an automated titration process using a linear ramp process.

FIG. 5 shows the results of this experiment. The pH reading is shown with a dashed line, with the scale on the left. The pump speed is shown as a solid line, with its scale on the right. The pump speed scale in FIG. 5 has been inverted in an attempt to make the cause and effect easier to follow when reading the graph, as increased pump speed will drive pH down. When observing graphs plotted in this style, one is cautioned to not try to infer too much by the relative positions of the two distinct curves. Since they have distinct scales, their relative positions are arbitrary. Here, they are superimposed so as to make time comparisons easier.

The stepwise progression of pump speed is readily apparent, and the pH reading is tracking direction. At the 12 minute mark, since the pH is below the target of 4.5, the measurement is terminated and the pump speed is returned to 0 rpm.

With knowledge of the pump rate required to achieve the target indicator, there exists sufficient information to determine the concentration of the flow stream using $C^S = C^R \cdot n_S/n_R \cdot f_R/f_S$.

To minimize reagent usage, it is beneficial to keep both the sample flow rate and the measurement frequency as low as is reasonable. The lowest reasonable sample flow rate is determined by a pair of factors. One, variability in this flow rate seen in the field can be caused by a number of factors (e.g., filters clogging/getting cleaned) and there is a need to keep the variability below the nominal flow rate. Two, peristaltic pumps result in uneven (pulsed) flow at sufficiently low pumping rates. For example, the instrument's nominal sample flow rate may be 10 gal/hr (gph); however, such a pump can make readings over a range of 5 gph to 15 gph.

Lowering measurement frequency is straightforward in practice. In fact, one can perform a reading at whatever frequency is desired. The tradeoff here is twofold. One, regulatory requirements often specify a limit in the time between readings that get logged for compliance purposes. Two, if the interest is in providing automatic alkalinity control based on the readings, the need for proper control will determine the necessary measurement frequency.

There may be issues with the stepwise linear ramp approach to reagent pump rate control such as: (i) the inherent resolution of a reading is limited by the step size (the increase in reagent flow from one step to the next); (ii) long (fixed) step durations may contribute to reagent flow well above the minimum required; and (iii) the linear ramp may not resilient to changes in the sample flow rate during the run. One solution to these issues is to use the binary search and step early termination, moving away from what is essentially a linear search for the equilibrium point to a binary search. At the same time, instead of a fixed step time, one can actively monitor the pH reading during a step and terminate it early when possible.

Figure 6:
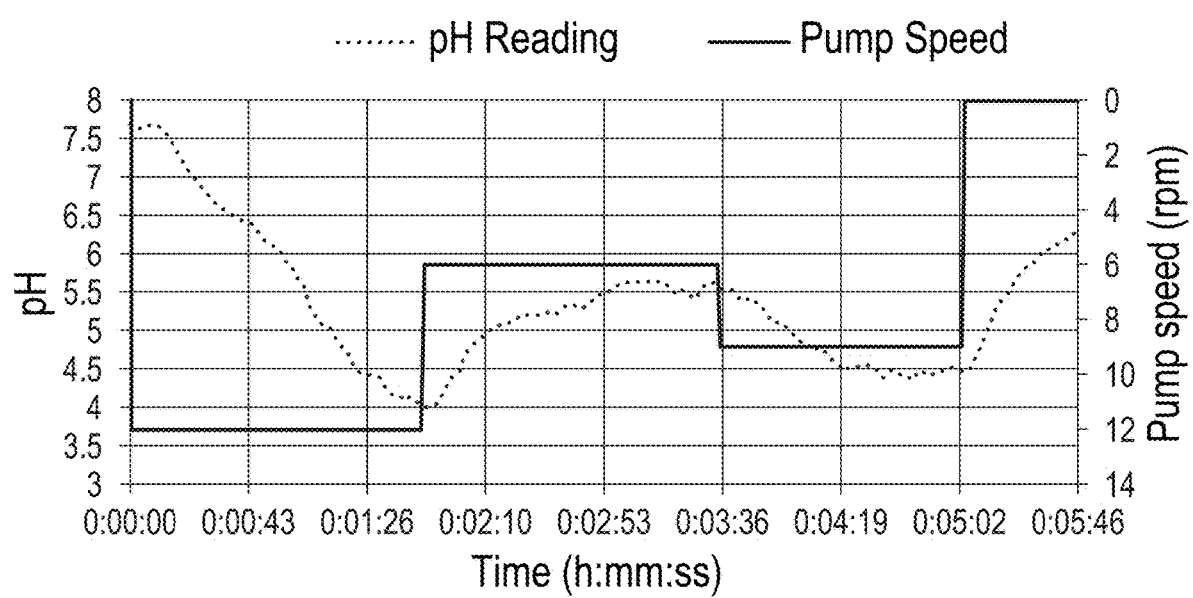
FIG. 6 is a graph illustrating the relationship between pump rates and measured indicator using the device of FIG. 3 in an automated titration process using a binary search and early step termination process.

FIG. 6 shows an experiment that encompasses both binary search and early step termination. At the beginning of the run, the reagent pump rate is set to the midpoint of its range (for example, 12 rpm, out of a range of 0 to 24 rpm supported by the pump). As the pH falls below 4, the step is terminated and the pump rate is set to 6 rpm. At time 3:36, the pH has climbed back above the target, so the pump rate is set to 9 rpm, which results in a pH right at 4.5. In general, the test is to see if the pH is within a settable error, E, of the target, i.e., one can consider the pH to be on target when $4.5 - \varepsilon \leq pH \leq 4.5 + \varepsilon$.

Early termination of a step is determined by the following. If it is a step that increases the pump rate, pH falling well below the target indicates that the pump rate can be decreased. Similarly, if it is a step that decreases the pump rate, pH rising well above the target gives us sufficient information to terminate the step. Finally, one can detect a stable pH reading by first passing the reading through a low-pass, finite impulse response filter whose coefficients are scaled so that the arithmetic can be performed using integer math. Taking a numerical derivative of this filtered pH signal results in an instability index. This index is compared to a threshold, which is used to indicate that the pH reading is sufficiently stable to terminate the step.

While the binary search technique with early termination helps address the first two issues identified with the stepwise linear ramp, it does nothing to address the third issue. The sample flow rate can range from 5 gph to 15 gph and the device is expected to function properly within this range.

In practice, the sample flow rate may not change rapidly over its entire range. For example, the flow rate may change a small amount during a reading, or there may be some external event which causes a significant flow rate change, but the flow is fairly stable after the change.

This behavior may be addressed in the binary search algorithm by incorporating a conditional back-off capability. If the maximum number of search steps have been executed, and the pH value is still not within c of the target, one can back up several steps in the search algorithm and re-engage the binary search with a wider scope. This back-off is repeated several times before the instrument reports an error that it is unable to complete a valid titration.

In another embodiment, it may not be necessary to wait until the pH reading stabilizes before the final value is reasonably known. When the reagent feed rate is initially changed, the response of the pH reading is exponential. With this knowledge, it is reasonable to take sufficient readings as to understand the exponential curve, extrapolate the final value, and move on to the next step immediately.

Figure 7:
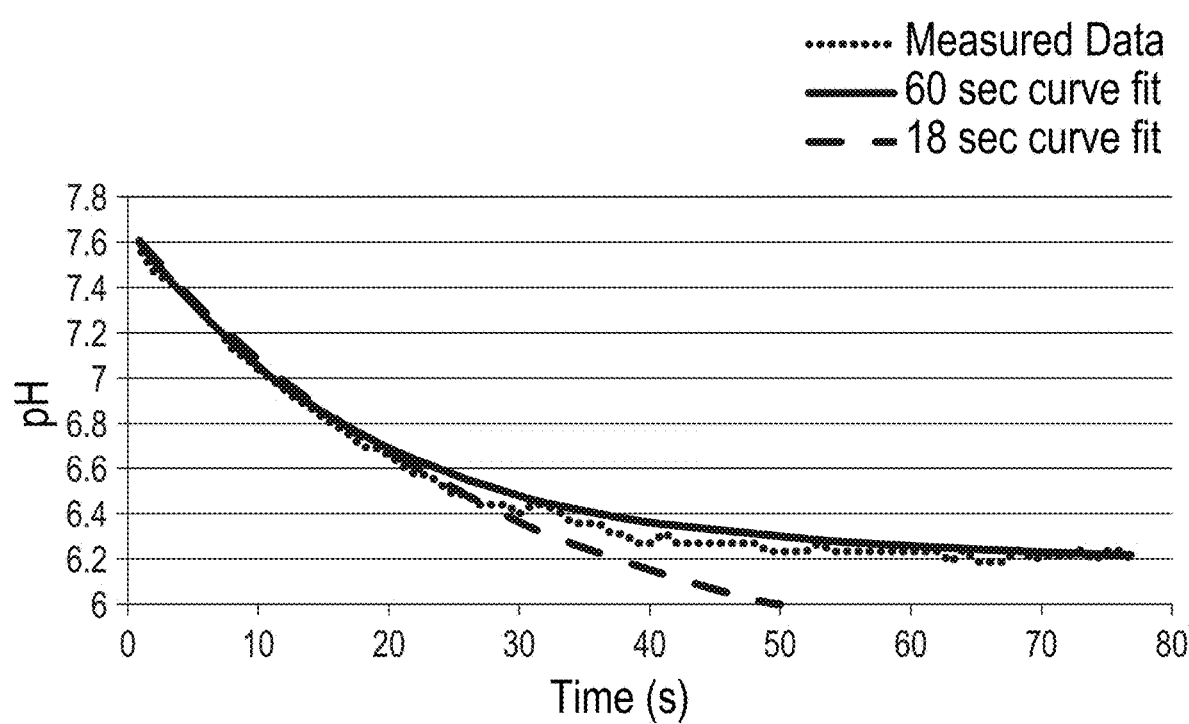
FIG. 7 is a graph illustrating a measured indicator over time using the device of FIG. 3 in an automated titration process in which one can extrapolate the indicator reading based on the exponential response.

FIG. 7 illustrates this effect, showing the time series of pH readings for just over one minute after a step change in the reagent feed rate. The pH value is read once per second. The solid curve represents an exponential curve fit to the first 60 seconds of the series, which results in the following expression for pH as a function of time: $pH=1.4e^{-t/18}+6.2$. Clearly, the final pH value of 6.2, at $t=\infty$ in this equation matches well with the actual value over 4 time constants out.

The alignment between the data and curve may not be particularly good at the beginning of the transition. If one performs an exponential curve fit just over the points in the first 18 seconds (essentially one time constant), the result is the following expression: $pH=2.0e^{-t/30}+5.6$. This curve is shown as the dashed line in FIG. 7. In this case, the final pH value of 5.6, at $t=\infty$, deviates significantly from the empirical data. The above is a particularly well behaved step response. As such, the current device does not attempt to exploit this property to further decrease reagent usage.

One of the techniques to reduce reagent usage is to decrease the measurement frequency. However, this has certain unwanted side effects. In the device 40 illustrated in FIG. 3, the tubing 44 used to feed the reagent may be a PVC material that has a fairly small inside diameter (e.g., about 2 mm) so as to support very low flow rates. In operation, the peristaltic pump 22 temporarily pinches the tubing 44 in sync with the stepper motor used with the pump 22. This pinch point moves along the length of the tubing 44 when reagent is flowing. When the pump is stopped (e.g., between titrations), the pinch point is stationary, and the tubing 44 remains pinched at this location until the subsequent titration run.

However, when the pump 22 is stopped for most of a day (which is the case when performing a single daily titration) the tubing 44 takes time to rebound from its pinched locations adjacent the rollers 52 to its original shape, and until that happens the actual flow rate through the pump 22 is reduced. This effect can sees in the experimental data presented in FIG. 6. Note that in the first step, the response of the pH reading looks much more linear than it does exponential. This is due to the recovery time required for the tubing 44 to return to its normal shape and function.

One solution to this complication is to not allow the pump 22 to completely idle. When the desired flow rate is zero, the rotor 62 may rock back and forth such that the locations of the pinched tubing 44 adjacent the rollers 52 vary along the tubing 44 so that no one position is pinched for an extended duration and, thus, the pinching stress is distributed over a length of the tubing 44.

Thus, described herein is a method and apparatus for automatic titration that has been developed to address the particular needs of recirculating water systems, including minimizing the quantity of reagent used. The reduction in reagent usage is accomplished by: (1) minimizing the sample flow rate; (2) minimizing the measurement frequency; (3) using a binary search algorithm to determine the reagent pump rate that matches the target indicator reading; and (4) terminating individual steps when the indicator reading is determined to be stable. In addition, the method and apparatus addresses the real effects of sample flow rates varying during a measurement, and the pump being idle for long durations having negative effects on the reagent tubing. The result is an apparatus that can repeatedly perform measurements in a recirculating water system.

Although certain illustrative embodiments and methods have been disclosed herein, it will be apparent from the foregoing disclosure to those skilled in the art that variations and modifications of such embodiments and methods may be made without departing from the spirit and scope of the invention. Accordingly, it is intended that the invention should be limited only to extent required by the appended claims and the rules and principals of applicable law.

The invention claimed is:

1. A method for determining a concentration of a chemical of interest in a recirculating system, the recirculating system comprising an analyte having a stoichiometric coefficient of $n_S$, the method comprising the steps of:
   (a) selecting a first indicator threshold;
   (b) measuring a flow rate of the recirculating system ($f_S$);
   (c) controllably adding a known amount of reagent having a stoichiometric coefficient of $n_R$ to the recirculating system at an reagent flow rate ($f_R$), wherein the reagent has a reagent concentration $C^R$;
   (d) repetitively measuring an indicator of the recirculating system downstream from the addition of the reagent, wherein the indicator is selected from the group consisting of pH and oxidation-reduction potential; and
   (e) computing the concentration of the chemical of interest in the recirculating system when the indicator crosses the first indicator threshold, wherein the concentration of the chemical of interest of the recirculating system is computed as: $C^S=C^R \cdot n_S/n_R \cdot f_R/f_S$.

2. The method of claim 1 wherein the analyte is an acid, the reagent is a base, and the indicator is pH, and wherein the concentration of the chemical of interest is computed when the indicator rises above the first indicator threshold.

3. The method of claim 1 wherein the analyte is a base, the reagent is an acid, and the indicator is pH, and wherein the concentration of the chemical of interest is computed when the indicator falls below the first indicator threshold.

4. The method of claim 1 wherein the analyte is a reducing agent, the reagent is an oxidizing agent, and the indicator is oxidation-reduction potential, and wherein the concentration of the chemical of interest is computed when the indicator rises above the first indicator threshold.

5. The method of claim 1 wherein the analyte is an oxidizing agent, the reagent is a reducing agent, and the indicator is oxidation-reduction potential, and wherein the concentration of the chemical of interest is computed when the indicator falls below the first indicator threshold.

6. The method of claim 1 wherein the step of controllably adding reagent to the recirculating system comprises the steps of:
   adding reagent at an initial reagent flow rate ($f_{R,INIT}$); and
   until the indicator measurement crosses the first indicator threshold, repetitively:
     measuring the indicator of the recirculating system; and
     increasing the reagent flow rate by a fixed increment; and
   setting $f_R$ equal to the reagent flow rate when the indicator measurement crosses the first indicator threshold for computing the concentration of the chemical of interest in the recirculating system.

7. The method of claim 6 further comprising:
   selecting a second indicator threshold that is less than the first indicator threshold; and
   if the measured indicator crosses the second indicator threshold, setting $f_R$ equal to the reagent flow rate when the indicator measurement crosses the second indicator threshold for computing the concentration of the chemical of interest in the recirculating system.

8. The method of claim 1 wherein the step of controllably adding reagent to the recirculating system comprises the steps of:
selecting a second indicator threshold;
selecting a duration of time;
adding reagent at an initial reagent flow rate;
calculating a difference between two successive indicator measurements; and
until the difference between two successive indicator measurements crosses the second indicator threshold for the set duration of time, repetitively:
measuring the indicator of the recirculating system; and
increasing the reagent flow rate by a fixed increment; and
setting $f_R$ equal to the reagent flow rate for computing the concentration of the chemical of interest in the recirculating system when the difference between two successive indicator measurements crosses the second indicator threshold for the set duration of time.

9. The method of claim 8 further comprising:
selecting a third indicator threshold that is less than the first indicator threshold; and
if the measured indicator crosses the third indicator threshold, setting $f_R$ equal to the reagent flow rate when the indicator measurement falls below the third indicator threshold for computing the concentration of the chemical of interest in the recirculating system.

10. The method of claim 1 wherein the step of controllably adding reagent comprises the steps of:
(a) adding reagent at an initial reagent flow rate;
(b) monitoring the measured indicator until the measured indicator exhibits an exponential response; and
(c) extrapolating a stable indicator reading based on the exponential response.

11. The method of claim 10 further comprising:
selecting a second indicator threshold that is less than the first indicator threshold; and
if the measured indicator crosses the second indicator threshold, setting $f_R$ equal to the reagent flow rate when the indicator measurement crosses the second indicator threshold for computing the concentration of the chemical of interest in the recirculating system.

12. The method of claim 1 wherein reagent is controllably added using a pump having a maximum and a minimum feed rate; and wherein the step of controllably adding reagent comprises the steps of:
selecting a tolerance of the first indicator threshold;
adding reagent at a reagent flow rate wherein the reagent flow rate is set to about an average of the maximum and minimum feed rates and, until the indicator measurement is within the tolerance of the first indicator threshold, repetitively:
comparing the measured indicator of the recirculating system to the selected first indicator threshold;
if the measured indicator is above the first indicator threshold, revising the minimum feed rate to the current reagent flow rate;
if the measured indicator is below the first indicator threshold, revising the maximum feed rate to the current reagent flow rate; and
resetting the reagent flow rate to about the average of the revised maximum and minimum feed rates.

13. The method of claim 12 further comprising:
selecting a second indicator threshold that is less than the first indicator threshold; and
if the measured indicator crosses the second indicator threshold, setting $f_R$ equal to the reagent flow rate when the indicator measurement crosses the second indicator threshold for computing the concentration of the chemical of interest in the recirculating system.

14. A device for determining a concentration of a chemical of interest in a recirculating system, the recirculating system comprising an analyte having a stoichiometric coefficient of $n_S$, comprising:
an intake port to receive a sample of the analyte;
a flow rate meter for measuring a flow rate of the sample of the analyte ($f_S$);
a vessel holding a reagent having a stoichiometric coefficient of $n_R$, wherein the reagent has a reagent concentration $C^R$;
a pump for controllably adding reagent from the vessel into the sample of the analyte at an reagent flow rate ($f_R$);
tubing for transferring the reagent from the pump to the sample of the analyte;
a probe for repetitively measuring an indicator of the recirculating system downstream from the addition of the reagent, wherein the indicator is selected from the group consisting of pH and oxidation-reduction potential; and
a computing element for computing the concentration of the chemical of interest in the recirculating system when the indicator measurement crosses an indicator threshold, wherein the concentration of the chemical of interest of the recirculating system is computed as: $C^S = C^R \cdot n_S/n_R \cdot f_R/f_S$.

15. The device of claim 14 further comprising a mixer for mixing the reagent into the sample of the analyte.

16. The device of claim 15, wherein the pump further comprises a rotor having a set of rollers capable of pinching the tubing in order to stop the transfer of reagent into the tubing.

17. The device of claim 16, wherein the rotor rocks back and forth such that the set of rollers pinches the tubing at different locations along a portion of the tubing when the pump is in an idle condition.

* * * * *